United States Patent

Meulenbrugge et al.

[11] Patent Number: 5,807,254
[45] Date of Patent: Sep. 15, 1998

[54] MAGNETIC RESONANCE DEVICE

[75] Inventors: Hendrik J. Meulenbrugge; Hans H. Tuithof; Johannes J. Van Vaals, all of Eindhoven, Netherlands

[73] Assignee: U.S. Philips Corporation, New York, N.Y.

[21] Appl. No.: 558,063

[22] Filed: Nov. 13, 1995

[30] Foreign Application Priority Data

Nov. 24, 1994 [EP] European Pat. Off. .............. 94203415

[51] Int. Cl.$^6$ .................................................. A61B 5/055
[52] U.S. Cl. ............................................. 600/411; 378/63
[58] Field of Search .............................. 128/653.1, 653.2; 324/307, 309; 378/62, 63; 600/407, 410, 411

[56] References Cited

U.S. PATENT DOCUMENTS

| | | | |
|---|---|---|---|
| 4,733,189 | 3/1988 | Ponchard et al. | 324/318 |
| 4,907,252 | 3/1990 | Aichinger et al. | 378/63 |
| 5,178,146 | 1/1993 | Giese | 128/653.2 |
| 5,318,025 | 6/1994 | Dumoulin et al. | 128/899 |
| 5,377,678 | 1/1995 | Dumoulin et al. | 128/653.1 |
| 5,398,684 | 3/1995 | Hardy | 128/653.2 |
| 5,485,839 | 1/1996 | Aida et al. | 128/653.1 |

FOREIGN PATENT DOCUMENTS

| | | |
|---|---|---|
| 3931854 | 4/1991 | Germany . |
| 4183446 | 6/1992 | Japan . |
| 5344964 | 12/1993 | Japan . |

Primary Examiner—Brian Casler
Attorney, Agent, or Firm—Jack D. Slobod

[57] ABSTRACT

A magnetic resonance device (1) for imaging inter alia human organs by way of magnetic resonance is provided in close proximity with an x-ray imaging device (20). When, for example, in neurosurgery interventional techniques are executed in combination with a magnetic resonance device (1), the organs are suitably visualized but the instruments guided to an organ via an opening in the body are not visible or only hardly so. Prior to the present invention, in order to carry out interventional procedures, the patient would be transported between a room housing magnetic resonance device and a room housing on x-ray device. Transporting the patient over a long distance between two rooms is objectional because of the risk of motion of the instruments lodged within the body of the patient; as such motion could be fatal to the patient. A solution consists in arranging an X-ray device (20) adjacent the MR device (1), so that the patient need be transported a short distance only. Undesirable mutual influencing of the MR device (1) and the X-ray device (20) is counteracted by shielding the static magnetic field of the MR device and the electromagnetic fields generated by the X-ray device.

4 Claims, 2 Drawing Sheets

MAGNETIC RESONANCE DEVICE

BACKGROUND OF THE INVENTION

1. Field of the Invention

The invention relates to a magnetic resonance device for imaging a part of an object by way of magnetic resonance, including a magnet system for generating a static magnetic field, means for generating RF electromagnetic signals and for generating temporary magnetic gradient fields so as to generate location-dependent magnetic resonance signals, a receiver unit for detecting the resonance signals, a reconstruction unit for processing the resonance signals received, a support for supporting the object to be imaged, and a control unit for generating control signals for the means for generating the RF electromagnetic signals and the temporary magnetic gradient fields.

2. Description of the Related Art

For the acquisition of information concerning the nuclear magnetization distribution by means of the above device, magnetic gradient fields are applied after successive RF pulses are generated in the static magnetic field by a coil. The resonance pulses generated by the RF pulses are received by the same coil or another coil and are applied to a reconstruction unit. Subsequently, the reconstruction unit processes the received signals so as to form images of the part of the object to be examined. The described magnetic resonance devices are used in the medical diagnostic field for the imaging of notably soft tissues in, for example human organs which contain large amounts of hydrogen nuclei.

It is a drawback of conventional magnetic resonance devices that instruments for carrying out interventional procedures within a patient, for example neurosurgery, cannot be imaged, or only hardly so, by means of the MR device. Therefore, for the imaging of the instruments use is made of an X-ray device which, however, does not produce images or only low-quality images of the organs to be treated. For the positioning of the instruments and the execution of interventions, therefore, it is necessary to have images available of the soft tissues, formed by means of the MR device, as well as of the instruments, formed by means of X-rays. Therefore, during interventional procedures the patient is moved to and fro between the MR device and the X-ray device in order to form the various images. However, because the conventional X-ray device is sensitive to magnetic stray fields generated by the magnet system of the MR device, the distance between an MR device and an X-ray device must be sufficiently large to enable acceptable images to be formed of the instruments lodged within the patient to be formed. Therefore, the X-ray device is arranged outside the shielding and hence outside the room in which the MR device is installed. During transport of the patient between the two imaging devices there is a risk of motion of the instruments within the patient due to jolting of the patient; such motions could be fatal to the patient. Moreover, the patient is connected to various other medical apparatus via tubes and other means, so that such transport is cumbersome.

SUMMARY OF THE INVENTION

It is inter alia an object of the invention to mitigate the necessity of transporting the patient, so that the risk of undesirable motions of the instruments within the body of the patient due to jolting during transport is reduced. It is a further object of the invention to simplify the integration of the coordinate systems of the MR device and the X-ray device, thus reducing the risk of errors in the guiding and positioning of the instruments relative to the organs to be treated.

The magnetic resonance device in accordance with the invention is characterized in that it also comprises an X-ray device which is arranged adjacent the MR device. As a result of this step, according to which the X-ray device is arranged within the same room at a distance of between 1 and 5 meters from the MR device and within the stray field of the static magnet system, the object, for example a patient arranged on the support, need only be transported over a comparatively small distance within the room in which the MR device is installed.

An embodiment of a device in accordance with the invention is characterized in that the MR device comprises a guide system via which the support can be moved to a first position and a second position, a part of the object being present in an imaging zone of the MR device in said first position whereas the part of the object is present in the imaging zone of the X-ray device in said second position. According to this step, MR images are made of the object, for example a patient, in the first position. X-ray images of the patient are made in the second position. Furthermore, this step reduces the risk of motion of the instruments within the patient due to jolting during transport, because the patient need be displaced in only a single direction, via the guide system, and remains on the same support. Furthermore, combination of the images of the MR device and the X-ray device requires only a transformation involving a translation along one axis. As a result, an accuracy in the millimeter range is achieved in the positioning of the patient and the instruments relative to both coordinate systems. The transport of the patient with the tubes and other connections is then also simplified.

A further embodiment of a device in accordance with the invention is characterized in that the X-ray device comprises a passive shield so as to counteract the influencing of the magnetic field of the MR device, which shield contains a material of high magnetic permeability. The X-ray device comprises an X-ray tube for generating X-rays and an X-ray image intensifier for converting an X-ray shadow image into a light image. Electron beams are generated in the X-ray tube as well as in the X-ray image intensifier. For suitable operation of the X-ray tube and the X-ray image intensifier it is necessary that the electron beams generated are not influenced by the static magnetic field of the MR device. The switched gradient fields of the MR device are not of importance, because they can be switched off during X-ray exposures. The effect of the static magnetic field on the electron beams generated in the X-ray device is reduced by installing the shield, so that the path of the electron beams is hardly affected and suitable operation of the X-ray device is possible.

A next embodiment of a device in accordance with the invention is characterized in that the MR device comprises means which counteract influencing of the X-ray apparatus. As a result of this step it is achieved that the MR device generates a weak static magnetic stray field, so that the X-ray device can be arranged at a comparatively small distance from the MR device.

Another embodiment of a device in accordance with the invention is characterized in that the X-ray device is arranged to counteract influencing of the MR device by electromagnetic radiation of the X-ray device. As a result of this step it is achieved that during formation of images by means of the MR device no disturbing effects are exerted by the X-ray device. This can be simply achieved by switching off the X-ray device.

A further embodiment of a device in accordance with the invention is characterized in that the reconstruction unit is arranged to carry out the following steps:

a) formation of images by the MR device, b) formation of images by the X-ray device, c) combination of location information of the images formed sub a) and b).

According to this step, information from the MR unit and from the X-ray device is processed in an alternating fashion and the images formed from this information are combined so as to form, for example one image with one reference coordinate system for display on, for example a monitor.

These and other aspects of the invention will be apparent from and elucidated with reference to the embodiments described hereinafter.

DETAILED DESCRIPTION OF THE PREFERRED EMBODIMENTS

Figure 1:
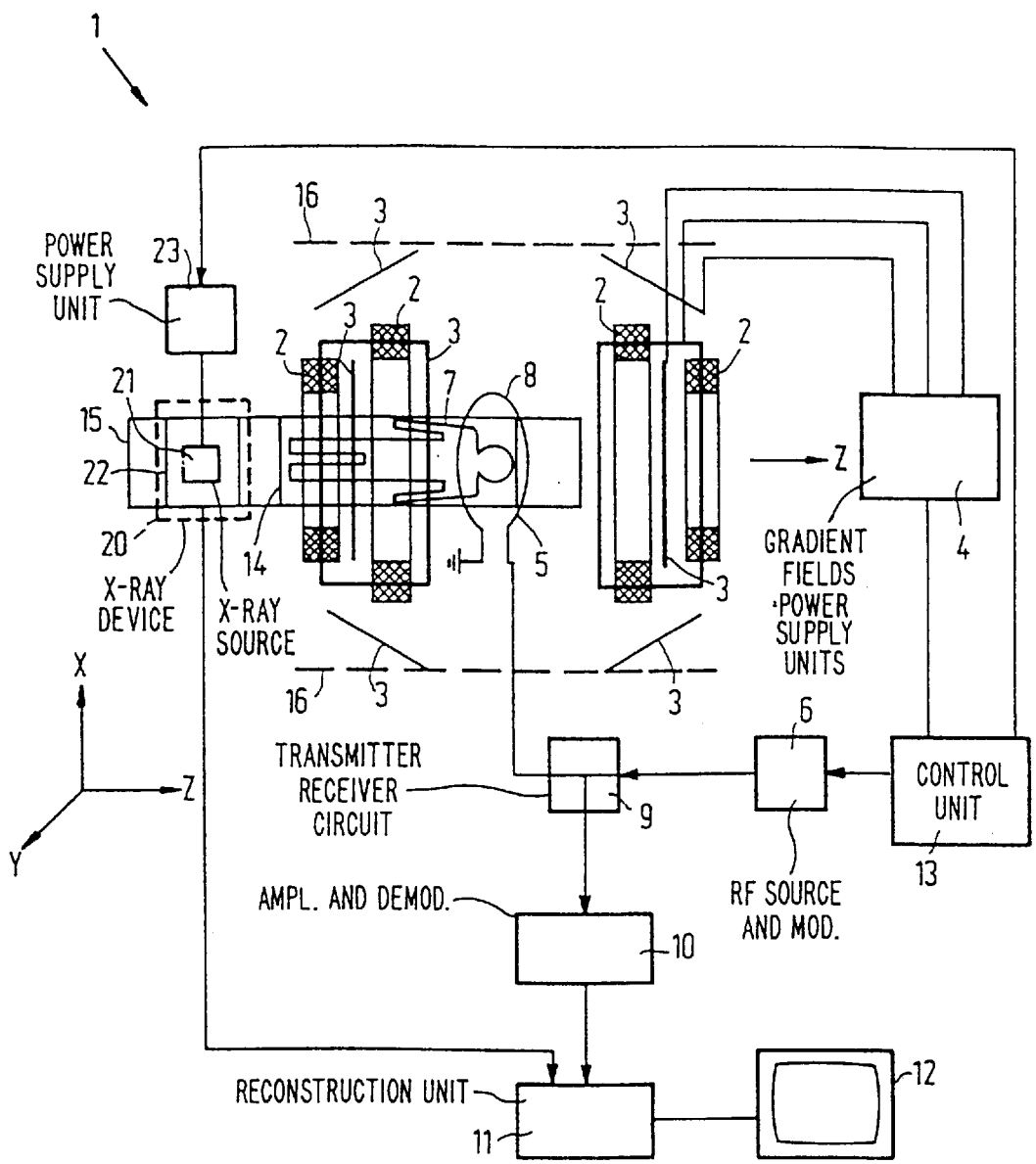
FIG. 1 shows an embodiment of an MR device and an X-ray device.

FIG. 1 shows a device in accordance with the invention, comprising a magnetic resonance device 1, for example a Gyroscan ACS NT as marketed by Philips Medical Systems, and an X-ray device 20, for example a BV 29 or BV 212 as marketed by Philips Medical Systems. The MR device 1 comprises a first magnet system 2 for generating a static magnetic field, a second magnet system 3 for generating gradient fields, and power supply units 4 for the first magnet system 2 and the second magnet system 3. The power supply unit for the first magnet system 2 is not shown. The magnet systems 2 and 3 are shielded by a shield 16. As is customary, in FIG. 1 and in this description the z-direction of the coordinate system shown corresponds to the direction of the static magnetic field in the magnet system 2. An RF transmitter coil 5 serves to generate RF magnetic fields and is connected to an RF source and modulator 6. Within the examination space the RF transmitter coil 5 is arranged around or against or near a part of the patient to be examined. A receiver coil 8 is used to receive the magnetic resonance signal. This coil may be the same coil as the RF transmitter coil 5. The transmitter/receiver coil 5 is connected, via a transmitter/receiver circuit 9, to a signal amplifier and demodulation unit 10. The phase and amplitude derived from this circuit are applied to a reconstruction unit 11. The reconstruction unit 11 processes the signals presented so as to form an image of a part of the patient; for example, this image is displayed on a monitor 12. The control unit 13 also controls a modulator 6 for the RF transmitter and the power supply units 4 for the magnetic gradient fields.

For the execution of interventional procedures, the X-ray device 20 is arranged adjacent the MR device 1. The X-ray device, therefore, is present in the same room as the MR device, and hence is situated within the static stray field of the magnets of the MR device. The distance between the MR device 1 and the X-ray device 20 is, for example 3 meters. The examination space of the MR device 1 and the examination space of the X-ray device 20 are situated one in the prolongation of the other. A guide system 15 is also installed in this room. On the guide system 15 there is arranged a displaceable support 15, for example a patient table on which a patient 7 is transported from the MR device 1 to the X-ray device 20 and vice versa. Because the support 14 is displaced along the z-axis of the coordinate system, the risk of jolting of the patient is reduced and the risk of motion of the instruments lodged within the body of the patient during an interventional procedure is also reduced.

The X-ray device 20 also comprises a power supply unit 23, an X-ray source 21 and an X-ray detector 22. During formation of an X-ray image, the X-ray source 21 in the X-ray device 20 generates an X-ray beam whereto the patient 7 in the examination space is exposed. An X-ray shadow image is formed on the entrance window of the X-ray detector 22 by absorption of the X-ray beam within the patient 7. The X-ray detector 22 subsequently generates electric image signals which are applied to the reconstruction unit 11. In the reconstruction unit 11 the information of these images is combined with the information of the images of the MR device 1 so as to be stored and displayed on, for example a monitor 12. For the combination of the images of the MR device 1 and the X-ray device 20, a transformation which comprises a translation places the coordinate systems of the images of the MR device and the X-ray device one onto the other in order to counteract errors in, for example the positioning of instruments within the patient.

Figure 2:
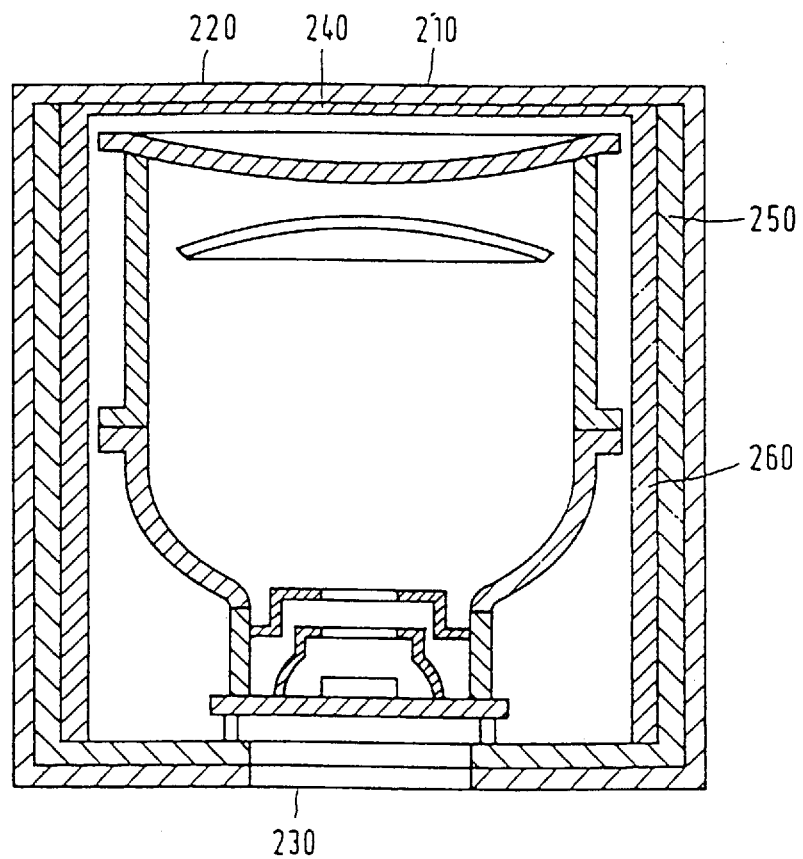
FIG. 2 shows an embodiment of an X-ray image intensifier provided with a magnetic shield.

The possibility of generating an X-ray image by means of conventional X-ray detectors arranged in the vicinity of an MR device is created by utilizing a passive shield for counteracting the static magnetic field of the MR device at the area of the X-ray detector 22, by utilizing an X-ray device which is quickly available for forming X-ray images after switching on, and by utilizing an MR device having a weak external magnetic stray field, for example the Philips Gyroscan ACS NT. One possibility of utilizing a passive shield is, for example to provide the X-ray image intensifier within the X-ray detector 22 with a shield containing a material of high magnetic permeability, for example soft iron. FIG. 2 shows an example of an X-ray image intensifier 200 with a shield. The X-ray image intensifier comprises a housing 210 with an entrance window 220 and an exit window 230. The inner side of the housing 210 is provided with a soft-iron shield 240. The layer thickness of the soft-iron shield 240 is, for example 0.1 mm. A shield of this thickness still offers a high X-ray transmittivity. Furthermore, the remainder 260 of the inner side of the housing 21 is provided with a soft-iron shield having a layer thickness of 1.5 mm. This layer thickness also offers X-ray shielding. Finally, the housing 210 is provided with a lead layer 250 for further attenuation of the X-rays.

We claim:

1. An imaging arrangement comprising:

a magnetic resonance (MR) device, including a magnet system for generating a static magnetic field and means for generating and for receiving MR signals; and an X-ray device comprising an X-ray source and an X-ray detector which internally generates an electron beam when in operation, which X-ray device is arranged adjacent the MR device within a stray magnetic field produced by said magnet system, and a passive magnetic shield means disposed about said X-ray detector containing a material of high magnetic permeability for substantially preventing said stray magnetic field from having an effect on said electron beam, wherein said X-ray detector is an X-ray image intensifier having an entrance window for receiving X-ray radiation and an exit window for transmitting optical radiation, and said shield means substantially surrounds said X-ray image intensifier except at said entrance and exit windows with a thick material of high magnetic permeability, and overlies the entrance window with a thin material of high magnetic permeability to allow X-ray radiation to pass therethrough, and a support for supporting an object during imaging of part of the object by the MR device and during imaging of the part of the object by the X-ray device.

2. An imaging arrangement as claimed in claim 1, further comprising a guide system via which the support can be moved to a first position and a second position, a part of the object being present in an imaging zone of the MR device in said first position and being present in an imaging zone of the X-ray device in said second position.

3. An imaging arrangement as claimed in claim 2, further comprising an image processing unit configured for forming an image obtained by using the MR device, forming an image obtained by using the X-ray device, and combining location dependent information of the formed image obtained by using the MR device with location dependent information of the formed image obtained by using the X-ray device to form a combined image.

4. An imaging arrangement as claimed in claim 1, further comprising an image processing unit configured for forming an image obtained by using the MR device, forming an image obtained by using the X-ray device, and combining location dependent information of the formed image obtained by using the MR device with location dependent information of the formed image obtained by using the X-ray device to form a combined image.

* * * * *